United States Patent [19]

Scopelianos

[11] Patent Number: 4,877,775

[45] Date of Patent: Oct. 31, 1989

[54] POLYMERIC AMINOSACCHARIDES AS ANTIHYPERCHOLESTEROLEMIC AGENTS

[75] Inventor: Angelo G. Scopelianos, Wilmington, Del.

[73] Assignee: E. I. Du Pont de Nemours and Company, Wilmington, Del.

[21] Appl. No.: 874,478

[22] Filed: Jun. 16, 1986

[51] Int. Cl.$^4$ .................. A61K 31/70; C07H 15/20
[52] U.S. Cl. ........................ 514/41; 514/36; 514/38; 514/39; 536/13.2; 536/13.3; 536/13.6; 536/13.7; 536/13.8; 536/16.6; 536/16.8
[58] Field of Search ............ 536/13.2, 13.3, 13.6, 536/13.7, 16.8, 20, 16.6; 514/39, 36, 55, 38, 41

[56] References Cited

U.S. PATENT DOCUMENTS

| | | | |
|---|---|---|---|
| 3,081,226 | 3/1963 | DiLuzio | 167/55 |
| 3,282,783 | 11/1966 | Vanderhaeghe | 167/65 |
| 3,350,387 | 10/1967 | Vanderhaeghe | 260/210 |
| 3,383,281 | 5/1968 | Wolf et al. | 167/65 |
| 3,499,960 | 3/1970 | Macek et al. | 424/33 |
| 3,627,872 | 12/1971 | Parkinson | 424/79 |
| 3,769,399 | 10/1973 | Hagerman | 424/79 |
| 3,780,171 | 12/1973 | Irmscher et al. | 424/79 |
| 3,787,474 | 1/1974 | Daniels et al. | 260/459 |
| 3,909,358 | 9/1975 | Stanley et al. | 195/63 |
| 3,974,272 | 8/1976 | Polli et al. | 424/78 |
| 3,980,770 | 9/1976 | Ingelman et al. | 424/79 |
| 4,035,146 | 7/1977 | Brenner et al. | 8/94.21 |
| 4,055,554 | 10/1977 | Helmstetter | 260/117 |
| 4,064,234 | 12/1977 | Howard | 424/157 |
| 4,089,746 | 5/1978 | Masri et al. | 195/63 |
| 4,094,743 | 6/1978 | Leuba | 195/63 |
| 4,125,708 | 11/1978 | Masri et al. | 536/20 |
| 4,198,395 | 4/1980 | DeSimone | 424/79 |
| 4,393,145 | 7/1983 | Zemp | 521/38 |
| 4,412,011 | 10/1983 | Kihara et al. | 521/38 |
| 4,436,731 | 3/1984 | Maltz | 424/18.0 |

FOREIGN PATENT DOCUMENTS

| | | |
|---|---|---|
| 12804 | 12/1978 | European Pat. Off. . |
| 0098884 | 1/1984 | European Pat. Off. . |
| 2227123 | 6/1971 | Fed. Rep. of Germany . |
| 147819 | 12/1979 | German Democratic Rep. . |
| 5246201 | 11/1977 | Japan . |
| 055979 | 5/1978 | Japan . |
| 56150017 | 4/1980 | Japan . |
| 58055418 | 9/1981 | Japan . |

OTHER PUBLICATIONS

*Burger's Medicinal Chemistry*, Fourth Ed., Part II, Ed. M. E. Wolff, Univ. of California, John Wiley & Sons, NY, pp. 218–226.

Remington's Pharmaceutical Sciences, Seventeenth Ed., 1985, pp. 1179–1183.

*Biochemistry*, 2nd Ed., "The Molecular Basis of Cell Structure and Function," A. L. Lehninger, Johns Hopkins Univ., pp. 249–272.

The Medical Letter, unknown date, pp. 74–76.

*Primary Examiner*—Johnnie R. Brown
*Assistant Examiner*—Elli Peselev

[57] ABSTRACT

Crosslinked copolymers of monomeric aminosaccharides such as aminoglycosidic antibiotics, e.g. neomycin, or of polymeric aminosaccharides, e.g., chitosan, with dialdehydes are useful antihypercholesterolemic agents due to their ability to bind with bile acids. These copolymers are insoluble in acidic solutions but are swellable to at least about 2× their original weight.

24 Claims, No Drawings

POLYMERIC AMINOSACCHARIDES AS ANTIHYPERCHOLESTEROLEMIC AGENTS

BACKGROUND OF THE INVENTION

1. Field of the Invention

This invention relates to polymeric aminosaccharides, processes for their preparation and their use as antihypercholesterolemic agents. More particularly, this invention relates to polymeric aminosaccharides which are high molecular weight nonabsorbable resins resulting from the crosslinking of monomeric or polymeric aminosaccharides and dialdehydes via Schiff's base formation followed by reductive amination to give non-hydrolyzable linkages.

2. Technical Background and Prior Art

Myocardial infarction, thrombosis, and stroke are the clinical sequalae of the underlying disease process of atherosclerosis. Collectively, these manifestations of Coronary Heart Disease (CHD) are at high levels and constitute the number one cause of death and disability in the United States, [R. I. Levy, *Arteriosclerosis*, 1, 312-325 (1981)]. Economically this loss is estimated at approximately $60 billion in direct health care costs, lost wages, and decreased productivity [Lipid Research Clinics Program, *J. Amer. Med. Assoc.*, 251, 351-364 (1984)]. Epidemiological studies have established the relationship of elevated plasma cholesterol and the incidence of CHD [W. B. Kannel et al. *Ann. Intern. Med.*, 90, 85-91 (1979) and The Pooling Project Research Group, *J. Chron. Dis.*, 31, 201-306 (1978)]. Moreover, the lipoprotein distribution of plasma cholesterol in low density lipoproteins (LDL-C) and high density lipoproteins (HDL-C) have been positively and negatively correlated with CHD, respectively [W. B. Kannel et al., *Circulation*, 70, 153-205A (1984)]. These observations have fostered the position that a reduction in plasma total and LDL-C through diet and/or drug therapy may be beneficial in the treatment of CHD.

Recently, several studies have been completed which have tested the efficacy of reducing plasma cholesterol through drug therapy and its impact on CHD [Lipid Research Clinics Program, *J. Amer. Med. Assoc.* 251, 351-364 (1984), J. F. Brensike, *Circulation*, 69, 313-324 (1984) and R. I. Levy at al., *Circulation*, 69, 325-337 (1984)]. The Lipid Research Clinics Coronary Primary Prevention Trial (LRC-CPPT) and the National Heart Lung and Blood Institute, Type II Coronary Intervention Study(NHLBI-CIS) both employed the bile acid sequestrant resin cholestyramine in combination with diet modification to lower circulating cholesterol levels. The results of the LRC-CPPT showed that a reduction in total plasma cholesterol by lowering LDL-C can reduce the incidence of CHD morbidity and mortality in men at risk for CHD [Lipid Research Clinics Program, *J. Amer. Med. Assoc.* 251, 351-364 (1984)]. The reduction in LDL-C and CHD was enhanced by drug treatment.

Similarly, the NHLBI-CIS results [J. F. Brensike, *Circulation*, 69, 313-324 (1984) and R. I. Levy et al., *Circulation*, 69, 325-337 (1984)], demonstrate that an increase in HDL-C and decreases in total and LDL-C are associated with lower CHD progression. These favorable lipid profiles were enhanced by cholestyramine therapy. In combination, these results strongly support the conclusion that bile acid sequestrant therapy is an effective means to retard the progression and clinical manifestations of CHD. This action is due to the favorable influence of the drug on the lipoprotein profile of individuals at risk for CHD.

Cholestyramine, an ion exchange resin, is essentially a styrene polymer containing quaternary ammonium groups crosslinked by divinylbenzene and is covered in U.S. Pat. Nos. 3,499,960 and 3,780,171 amongst others. The mechanism for reducing blood cholesterol levels is through absorption of bile acids in the intestinal tract which prevents the circulation of bile acids. Hepatic cholesterol is thereby converted to bile acid, resulting in increased hepatic clearance and lower cholesterol levels in the blood.

Cholestyramine has a gritty consistency and has an unpleasant odor inherent to aliphatic amines, both of which lead to poor patient compliance. Also, it may cause rash and irritation as well as gastrointestinal distress. In addition, it has the drawback that other drug substances and vitamins are also removed by adsorption.

Thus, there is a need for new products which would be useful in bile acid sequestrant therapy which are less gritty, odorless, and which are generally more palatable with fewer side effects than cholestyramine.

SUMMARY OF THE INVENTION

According to the present invention, crosslinked polymers are provided which comprise at least one reduced copolymer of a monomeric or polymeric aminosaccharide and a dialdehyde or a pharmaceutically acceptable salt thereof.

This invention also provides pharmaceutical compositions suitable for oral administration containing as active ingredient at least one of the aforesaid crosslinked polymers together with a pharmaceutically suitable carrier. The compositions can also contain additional therapeutic agents such as clofibrate, or niacin which are systemic hypocholesterolemic agents.

The crosslinked polymers used in compositions of this invention are those described below which bind bile acids in the gastrointestinal tract so that they cannot be reabsorbed by the intestines and are excreted in the feces.

Further provided are methods for treating hypercholesterolemia in a mammal comprising administering orally an effective amount of at least one of the aforesaid crosslinked polymers which have a high affinity for binding bile acids.

Also provided are processes for preparing the aforesaid crosslinked polymers of this invention comprising contacting a polyamine antibiotic or aminopolysaccharide with a dialdehyde to form a crosslinked polymer via Schiff's base formation followed by reductive amination of the hydrolytically unstable Schiff's base to form a reduced polymer containing —$CH_2NH$— bonds.

DETAILED DESCRIPTION OF THE INVENTION

The polymers of this invention are semisynthetic, high molecular weight, nonabsorbable polymers which result from the reaction of a monomeric or polymeric aminosaccharide with a suitable dialdehyde, followed by reduction to crosslink the polymer. In particular, the monomeric aminosaccharides useful in this invention are the 2-deoxystreptamine aminoglycosidic antibiotics, including the neomycins, kanamycins, paromomycins, gentamycins and tobramycins; the structures of which are known. See: The Merck Index, Ninth Edition, 1976;

Burger's Medicinal Chemistry, 4th Ed. Part II p. 218-226.

The above 2-deoxystreptamine aminoglycosides are characterized by the presence of one or more amino sugars, such as glucosamine or neosamine, linked by a glycoside linkage to a deoxystreptamine moiety. The resulting polymers are derivatives of the above antibiotics wherein the majority of the amino groups have been crosslinked. The resulting highly crosslinked polymers, unlike the monomeric precursors and unreduced polymers, are devoid of antibacterial activitiy by virtue of this crosslinking.

The polymeric aminosaccharides useful in this invention include natural biopolymers such as chitin, chitosan and the mucopolysaccharides. Mucopolysaccharides as defined in "Biochemistry," Lehninger; a standard text in the field of Biochemistry, are heteropolysaccharide usually containing two types of alternating monosaccharide units of which at least one has an acidic group, either a carboxyl or sulfuric group.

Among useful dialdehydes are those prepared from polycarboxylic acids having the general formula $OHC(CH_2)_xCHO$ where X is 0-7, preferably 0-5, or 1-7 or 1-5 when a monomeric antibiotic is used. These dialdehydes are glyoxal, malonic aldehyde, succinic aldehyde, glutaraldehyde, adipic aldehyde, and pimelic aldehyde. Of these, glyoxal and glutaraldehyde are preferred; provided, however, that glyoxal is not used to prepare a crosslinked polymer of an aminoglycoside antibiotic.

Aromatic dialdehydes can also be used. Among these there are phthalic aldehyde, isophthalic aldehyde and terephthalic aldehyde.

Unsaturated dialdehydes such as maleic aldehyde and fumaric aldehyde can also be used. As would be expected, the double bond in the dialdehyde is also reduced when the Schiff's base is reduced to form a crosslinked polymer containing —$CH_2NH$— bonds.

Preferred polymers are reduced copolymers of neomycin sulfate or kanamycin monosulfate and glutaraldehyde. Also preferred are reduced copolymers of chitosan and glutaraldehyde or chitosan and glyoxal.

The synthesis of the polymers of this invention is accomplished by reacting one molar equivalent of an aminoglycoside or aminopolysaccharide with a twofold to sixfold excess of a suitable dialdehyde in an aqueous solvent such as water, aqueous acetic acid, aqueous methanol or the like, at a reaction temperature in the range of about 0° C. to 50° C., preferably at about room temperature. The Schiff's base which is formed is reduced in situ with a suitable reducing agent such as a borohydride, (i.e. sodium cyanoborohydride or N,N,N',N',N''-pentamethyldiethylenetriamine sodium tetrahydridoborate) preferably a twofold to tenfold excess of sodium cyanoborohydride ($NaCNBH_4$). The period within which the reaction goes to completion is determined by the nature of the reactants, temperature and solvent system employed, but generally the reaction is substantially complete in 4 hours.

Alternatively, the Schiff's base can be isolated and then reduced with a reducing agent such as sodium cyanoborohydride ($NaCNBH_4$), sodium borohydride ($NaBH_4$) or lithium aluminum hydride ($LiAlH_4$) in an inert solvent such as tetrahydrofuran, ether, methylene chloride, or the like.

More specifically, the reaction conditions for the preparation of preferred polymeric materials of this invention include the interaction of one molar equivalent of neomycin sulfate with a twofold to sixfold excess of glutaraldehyde, preferably fivefold, followed by reduction with a twofold to tenfold excess of $NaCNBH_3$, preferably 6.25 fold. Similarly, it is preferred to react one molar equivalent of kanamycin monosulfate with a twofold to fivefold excess of glutaraldehyde, preferably fourfold, and reduce with a twofold to tenfold excess of $NaCNBH_3$, preferably eightfold. The crosslinking of chitosan can be achieved in the presence of one to three molar equivalent excess of either glutaraldehyde or glyoxal. The reducing agent can also be used in the range of one to threefold excess.

When an aminopolysaccharide such as chitosan is employed, the synthesis is essentially the same as for neomycin sulfate but the order of addition of the reducing agent and the dialdehyde is reversed.

The polymers of the invention are easily transformed into the corresponding quaternary salts, such as ammonium halides, i.e., chlorides, bromides, iodides, using methods well known in the art such as reaction with an appropriate alkyl halide. Of the effective agents in quaternary ammonium form, the quaternary ammonium chlorides are most preferred.

The polymers of the invention are highly crosslinked and insoluble in all solvents tested, including tetrahydrofuran, acetonitrile, dimethylformamide, dimethyl sulfoxide, methanol, acetone, and toluene; and are characterized by being insoluble in aqueous solutions of pH 1-8 but are swellable at least $2\times$, preferably about $4-5\times$ their original weight therein. When filtered and washed, analysis shows no residual monomers, i.e., the monomeric or polymeric aminosaccharide and the dialdehyde. In addition, the aminoglycosidic antibiotics lose their antibacterial properties.

It will be appreciated that there are several advantages to the polymers of the present invention. The polymers are tasteless and do not have the unpleasant odor associated with quaternary amines. They are very pliable when hydrated, compared to the gritty consistency of cholestyramine. Furthermore, because of the crosslinked nature of the polymers, absorption into the blood stream is minimal. The crosslinking is via non-hydrolyzable bonds, i.e., amine bonds rather than easily hydrolyzed amide or ester linkages, and therefore are inert to degradation by digestive enzymes resulting in polymers which lower plasma cholesterol without entering the systemic circulation.

The following examples will serve to further illustrate the present invention, but should not constitute a limitation thereof. Parts and percentages are by weight and temperatures in degrees Celsius unless otherwise indicated.

EXAMPLES 1a-1c

Neomycin sulfate (2 g) was dissolved in 20 ml of water. Glutaraldehyde (3.6-5.4 g of 25% aqueous solution) was added to the water solution of neomycin sulfate and stirred for 20 minutes. Addition of 0.55-0.83 g of sodium cyanoborohydride resulted in a yellow precipitate which was diluted with 140 ml of water and stirred for 4½ hours. The mixture was filtered and the precipitate was resuspended and refiltered from (a) $2\times100$ ml of water, (b) $2\times100$ ml of 0.1N hydrochloric acid, and (c) $2\times100$ ml of water. The washed solid was dried in vacuo at 55°.

For the polymer of Example 1b, m.p. >200° C. (starts to char); IR (KBr): 3600-3000 cm$^{-1}$ (OH and NH), 2940 cm$^{-1}$ (CH), 1630 cm$^{-1}$ (+NH), 1050 cm$^{-1}$ (1°—OH). Anal: Calc. for $(C_{41}H_{82}N_6O_{13}Cl_6)_x$; C, 45.60; H, 7.65; N, 7.78: Found: C, 46.79; H, 7.96; N, 7.90.

For in vitro results on binding of bile acids, see Table 1.

EXAMPLES 2a–2c

Chitosan (2 g) was dissolved in 100 ml of 2% aqueous acetic acid. Sodium cyanoborohydride (1.25–3.75 g) was added and stirred for 3 minutes before 4–12 ml of 25% glutaraldehyde was added. An immediate gelatin occurred. Water (350 ml) was added to suspend the gel and stirring was continued for 2 hours followed by gravity filtration through cheesecloth. The solids were resuspended and filtered from (a) 2×300 ml of 0.1N-HCl, and (b) 2×300 ml of water. The washed solid was dried in vacuo at 55°.

For the polymer of Example 2c, m.p. >200° C. (starts to char); IR (KBr): 3600–3000 cm$^{-1}$ (OH and NH), 2900–2800 cm$^{-1}$ (CH), 1650 cm$^{-1}$ (+NH), 1075 cm$^{-1}$ (1°—OH). Anal: Calc. for $(C_{22}H_{42}N_2Cl_2O_8)_x$; C, 49.81; H, 7.92; N, 5.28; Cl, 13.20. Found: C, 48.70; H, 7.89; N, 5.25; Cl, 13.15.

For in vitro results on binding of bile acids, see Table 2.

EXAMPLES 3a–3c

Chitosan (2 g) was dissolved in 100 ml of 2% aqueous acetic acid. Sodium cyanoborohydride (1.25–3.75 g) was added and stirred well for 3 minutes before 1.45–4.35 ml of 40% glyoxal was added. An immediate gelatin occurred. Water (350 ml) was added to suspend the gel and stirring was continued for 2 hours followed by gravity filtration through cheesecloth. The solids were resuspended and filtered from (a) 2×300 ml of 0.1N HCl, and (b) 2×300 ml of water. The washed solid was dried in vacuo at 55°.

For the polymer of Example 3a, m.p. >180° C. (starts to char); IR (KBr): 3600–3000 cm$^{-1}$ (OH and NH), 2950 cm$^{-1}$ (CH), 1645 cm$^1$ (+NH), 1050 cm$^{-1}$ (1°—OH).

For in vitro results on binding of bile acids, see Table 3.

EXAMPLES 4a–4c

Kanamycin monosulfate (2 g) was dissolved in 20 ml of water. Glutaraldehyde (4.2–7.0 ml of 25% aqueous solution) was added to the water solution and stirred for 20 minutes. Addition of 1.28–2.14 g of sodium cyanoborohydride resulted in a yellow-orange precipitate which was diluted with 300 ml of water and stirred for 4½ hours. The mixture was filtered and the precipitate was resuspended and refiltered from (a) 2×350 ml of water, (b) 2×350 ml of 0.1N hydrochloric acid, and (c) 2×350 ml of water. The washed solid was dried in vacuo at 55°.

For the polymer of Example 4b, m.p. >170° C. (starts to char); IR (KBr): 3600–3000 cm$^{-1}$ (OH and NH), 2940 cm$^{-1}$ (OH), 1635 cm$^{-1}$ (+NH), 1050 cm$^{-1}$ (1°—OH).

For in vitro results on binding of bile acids, see Table 4.

IN VITRO STUDIES

Forty milligrams of each binding substance of Examples 1–4 were mixed with 100 μ moles of a radioactive bile salt described in Tables 1–4 in 5 ml physiological saline (pH 7.0). These mixtures were incubated in sealed tubes for 1 hour at 37° with stirring. After incubation, the tubes were centrifuged at 32,000×g for 15 minutes. Aliquots (0.10 ml) of the supernatant were added to 7 ml of scintillation mixture and radioactivity was determined in a liquid scintillation spectrometer. Tables 1 through 4 summarize the in vitro results on binding to bile acids for the polymers of Examples 1–4.

TABLE 1

| | Binder | | | % μ moles Bound/ 40 mgs. of Binder | | |
|---|---|---|---|---|---|---|
| Ex. No. | Neomycin Sulfate (g) | Glutaraldehyde (25%) (ml) | NaCNBH$_3$ (g) | Cholate | Glyco-cholate | Tauro-cholate |
| 1a | 2.0 | 3.6 | 0.55 | 70 | 72 | 79 |
| 1b | 2.0 | 4.5 | 0.69 | 86 | 78 | 83 |
| 1c | 2.0 | 5.4 | 0.83 | 75 | 75 | 83 |

TABLE 2

| | Binder | | | % μ moles Bound/ 40 mgs. of Binder | | |
|---|---|---|---|---|---|---|
| Ex. No. | Chitosan (g) | Glutaraldehyde (25%) (ml) | NaCNBH$_3$ (g) | No. Cholate | Glyco-cholate | Tauro-cholate |
| 2a | 2.0 | 4 | 1.25 | 87 | 71 | 78 |
| 2b | 2.0 | 8 | 2.50 | 85 | 69 | 79 |
| 2c | 2.0 | 12 | 3.75 | 87 | 66 | 75 |

TABLE 3

| | Binder | | | % μ moles Bound/ 40 mgs. of Binder | | |
|---|---|---|---|---|---|---|
| Ex. No. | Chitosan (g) | Glyoxal (40%) (ml) | NaCNBH$_3$ (g) | Cholate | Glyco-cholate | Tauro-cholate |
| 3a | 2.0 | 1.45 | 1.25 | 90 | 72 | 73 |
| 3b | 2.0 | 2.90 | 2.50 | 94 | 70 | 72 |
| 3c | 2.0 | 4.35 | 3.75 | 91 | 70 | 71 |

TABLE 4

| | Binder | | | % μ moles Bound/ 40 mgs. of Binder | | |
|---|---|---|---|---|---|---|
| Ex. No. | Kanamycin (g) | Glutaraldehyde (25%) (ml) | NaCNBH$_3$ (g) | Cholate | Glyco-cholate | Tauro-cholate |
| 4a | 2.0 | 4.2 | 1.28 | 82 | 69 | 73 |

TABLE 4-continued

| | | | | | | |
|---|---|---|---|---|---|---|
| 4b | 2.0 | 5.6 | 1.71 | 85 | 71 | 74 |
| 4c | 2.0 | 7.0 | 2.14 | 88 | 79 | 82 |
| Control | | | | | | |
| Cholestyramine | | | | 76 | 70 | 82 |

The in vitro binding affinities for cholic, glycocholic and taurocholic acids are equivalent or superior to that of the Cholestyramine Control.

IN VIVO ASSESSMENT OF BILE ACID BINDING GENERAL PROTOCOL

Male Sprague-Dawley Rats were used exclusively during the protocols described. Animals were housed in a room with alternating light cycle of 12 h light and 12 h dark and were allowed free access to both food and water. Animals were sacrificed at the midpoint of the dark cycle by decapitation and livers were perfused in situ with 100 ml of cold 0.25M sucrose. Livers were removed and homogenized in 3 volumes of homogenization buffer as described [Trzaskos, et al., *J. Biol. Chem.*, 259, 13402–13412 (1984)]. Microsomes were isolated by centrifugation of the postmitochondrial supernatant also as described in the above publication and were stored at −80° C. until use.

3-Hydroxy-3-methylglutaryl-Coenzyme A reductase (HMGR) activity was determined on microsomal pellets as described by Philipp and Shapiro, *J. Lipid. Res.*, 20, 588–593 (1979). Dihydrolanosterol (DHL) demethylase activity was assayed as described by Trzaskos et al. Cholesterol 7α-hydroxylase activity was determined essentially as described by Nimmannit and Porter in *Arch. Biochem. and Biophysics*, 201, 533–544 (1980) employing [4-14C]cholesterol as substrate. Substrate was suspended with the aid of the detergent Triton ® WR-1339. Fecal bile acid levels were determined enzymically on acidic methanol extracts of stool samples employing 3α-hydroxysteroid dehydrogenase as described by van den Ende et al. in *Clinica Chemica Acta.*, 121, 95–109 (1982).

EXPERIMENT 1

Animals were divided into four groups with three animals per group and were fed one of four diets: Diet A, standard laboratory rodent chow plus 5% (w/w) corn oil; Diet B, Diet A containing 3% (w/w) cholestyramine; Diet C, Diet A plus 3% (w/w) neomycin; Diet D, Diet A plus 3% (w/w) crosslinked neomycin polymer of Example 1b. Animals were fed the diet ad libitum for four days. At the end of the feeding period, stool samples from each group were collected and pooled for bile acid analysis; rats were sacrificed and hepatic enzyme activities were determined. Food consumption was also monitored by the difference in total weight of prepared diet at the start and end of the study. Results are shown in Table 5.

EXPERIMENT 2

Animals were placed in one of five groups again with three animals per group and were fed one of several diets: Diet A, standard laboratory rodent chow plus 5% (w/w) corn oil; Diet B, Diet A plus 3% (w/w) cholestyramine; Diet C, Diet A plus 3% (w/w) crosslinked neomycin polymer of Example 1b; Diet D, Diet A plus 1.5% (2/2) crosslinked neomycin polymer of Example 1b; Diet E, Diet A plus 0.75% (w/w) crosslinked neomycin polymer of Example 1b. Animals were fed the diet ad libitum for four days. At the end of the feeding period, fecal bile acid analysis, hepatic enzyme activity measurements and food consumption were determined as described above.

Results are shown in Table 6.

The protocols described above were designed to assess in vivo bile acid binding efficiencies of the neomycin polymer by measuring hepatic sterol biosynthetic enzymes as well as fecal bile acid excretion. The rat is known to respond to a decrease in bile acid reabsorption by increasing cholesterol and bile acid biosynthesis. This response is reflected in induction of the biosynthetic enzymes which were chosen to monitor.

In vivo binding of bile acids by the neomycin polymer is demonstrated in Table 5. The neomycin polymer enhances fecal bile acid excretion over fivefold in the experimental group. The observed enhancement is greater than that seen for cholestyramine in the same study. The enhanced excretion of fecal bile acids is also reflected in induction of hepatic sterol biosynthetic enzymes. Both cholesterol as well as bile acid biosynthetic enzymes are increased in the experimental groups receiving the sequestrant resins.

Experiment 2 (Table 6) demonstrates that low levels (>0.75% w/w) of the crosslinked neomycin polymer are sufficient to bind bile acids in vivo. Excretion of fecale bile acids is saturated at low levels of the polymer in the diet. The extent of saturation and dose dependence of the binding capacity is best observed in the induction of enzyme activities which reflect quite accurately the loss of bile acids in treated animals.

TABLE 5

IN VIVO ASSESSMENT OF SEQUESTRANT POLYMERS UPON HEPATIC ENZYMES AND FECAL BILE ACID EXCRETION

| Diet | [1]Enzyme | | | [2]Bile Acid ($\mu$mol/gm) |
|---|---|---|---|---|
| | HMG-CoA reductase | Cholesterol 7α-hydroxylase (pmol/min/mg) | DHL 14α-demethylase | |
| (A) Control | 695 ± 97 | 13.3 ± 3.8 | 675 ± 180 | 2.8 ± 1.8 |
| (B) 3% Cholestyramine | 1474 ± 275 | 43.3 ± 7.1 | 1035 ± 95 | 11.1 ± 3.4 |
| (C) 3% Neomycin monomer | 904 ± 138 | 19.6 ± 11.7 | 625 ± 185 | 5.5 ± 0.01 |
| (D) 3% Neomycin | 55.8 ± 11.3 | 1075 ± 75 | 16.0 ± 1.5 | 1579 ± 287 |

TABLE 5-continued

IN VIVO ASSESSMENT OF SEQUESTRANT POLYMERS
UPON HEPATIC ENZYMES AND FECAL BILE ACID EXCRETION

| Diet | [1]Enzyme | | | [2]Bile Acid (μmol/gm) |
|---|---|---|---|---|
| | HMG-CoA reductase | Cholesterol 7α-hydroxylase (pmol/min/mg) | DHL 14α-demethylase | |
| Polymer | | | | |

[1]per mg of microsomal protein
[2]per g of stool

TABLE 6

IN VIVO ASSESSMENT OF SEQUESTRANT POLYMERS
UPON HEPATIC ENZYMES AND FECAL BILE ACID EXCRETION

| Diet | [1]Enzyme | | | [2]Bile Acid (μmol/g) |
|---|---|---|---|---|
| | HMG-CoA reductase | Cholesterol 7α-hydroxylase (pmol/min/mg) | DHL 14α-demethylase | |
| (A) Control | 639 ± 116 | 23.2 ± 4.4 | 892 ± 266 | 14.7 ± 1.5 |
| (B) 3% Cholestyramine | 2734 ± 841 | 78.4 ± 6.5 | 1408 ± 59 | 20.0 ± 4.0 |
| (C) 3% Neomycin Polymer | 1601 ± 459 | 65.8 ± 15.2 | 1362 ± 46 | 25.9 ± 7.5 |
| (D) 1.5% Neomycin Polymer | 1016 ± 138 | 64.7 ± 6.3 | 1258 ± 77 | 23.6 ± 3.0 |
| (E) 0.75% Neomycin Polymer | 546 ± 23 | 39.8 ± 7.0 | 943 ± 138 | 12.1 ± 2.0 |

[1]per mg of microsomal protein
[2]per g of stool

ASSESSMENT OF BILE ACID SEQUESTRANT POLYMERS UPON HAMSTER PLASMA CHOLESTEROL LEVELS PROTOCOL

Male Syrian Hamsters weighing 125-145 gm were housed in a room with alternating light cycle of 12 h light and 12 h dark and were fed a diet containing cholesterol (0.24%, w/w) for two weeks. Animals were bled by retro-orbital techniques and plasma cholesterol values were determined by the method of Rudel and Morris [J. Lipid Research 14, 364-366 (1973)]. Animals were then divided into six groups with equal mean cholesterol values and were fed one of the six following diets: (A) chow plus 0.24% cholesterol (w/w); (B) Diet A containing 0.5% Cholestyramine (w/w); (C) Diet A containing 0.5% neomycin polymer (w/w) of Example 1b; (D) Diet A containing 0.5% Chitosan (w/w); (E) Diet A containing 0.5% crosslinked Chitosan (w/w) of Example 2b; (F) Diet A containing 0.5% crosslinked Chitosan (w/w) of Example 2c. The diets were fed for an additional two weeks when plasma cholesterol values were again determined by the above techniques.

RESULTS

The effect of the various diet protocols upon plasma cholesterol levels in the six hamster groups are shown in Table 7. As expected, the plasma cholesterol level in the control group (Diet A) increased during the second two week feeding period. This amounted to a 94 mg/dl increase. By comparison, animals in the various experimental groups displayed a range of increases in plasma cholesterol values. In all cases, the increase was lower than that of the control group, and in two cases there was an actual decrease in the plasma cholesterol level when compared to the two week control bleed (see Diets C and F). When the plasma cholesterol level of the diet groups B-F were compared to the control Diet A group, only the neomycin diet group was significantly different at P=0.05.

The trends indicate, however, that there was an effect of all the diets on the plasma cholesterol level. This trend was to prevent the increase in plasma cholesterol observed in the control group. The two polymers in Diets C and F mentioned above again show the greatest effect. The neomycin polymer was the only sequestrant which prevented the rise in plasma cholesterol significantly at P=0.05 when compared to the control group.

These data demonstrate that in the cholesterol-fed hamster that the various sequestrant polymers do act as antihypercholesterolemic agents. The results also show that the crosslinked neomycin polymer is most effective in this regard with the Chitosan of Example 2c running second in this analysis. Both compounds are more effective than Cholestyramine, which is the standard employed in the analysis.

TABLE 7

PLASMA CHOLESTEROL VALUES OF CHOLESTEROL-FED HAMSTERS ON VARIOUS SEQUESTRANT DIETS

| Diet | Cholesterol Level[1] | | Increase |
|---|---|---|---|
| | mg/dl | | |
| (A) 0.24% (w/w) Cholesterol | | | |
| 2 wk. bleed | 288 ± 6 | (36) | — |
| 4 wk. bleed | 382 ± 78 | (6) | 94 |
| (B) 0.5% Cholestyramine | 321 ± 28 | (6) | 33 |
| (C) 0.5% Neomycin Polymer (Ex. 1b) | 252 ± 12 | (6)* | −36* |
| (D) 0.5% Chitosan | 322 ± 34 | (6) | 34 |
| (E) 0.5% Chitosan Polymer (Ex. 2b) | 321 ± 38 | (6) | 33 |
| (F) 0.5% Chitosan Polymer (Ex. 2c) | 278 ± 18 | (6) | −10 |

[1]Mean ± SEM; numbers in parentheses represent animals per group.
*Significant at P = 0.05, when compared to control 4 wk. bleed.

Dosage Forms:

The polymers of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. Preferred because of the high dose required and swelling (hydration) characteristics of the active ingredient are powders, granules and semi-solid dosage formulations. The active ingredient can be administered alone, but is generally administered with a pharmaceutical carrier.

The dosage administered will, of course, vary depending upon known factors such as the age, health, and weight of the recipient; nature and extent of symptoms, kind of concurrent treatment, frequency of treatment, and the effect desired. Usually a daily dosage of active ingredient can be up to about 25 to 30 grams and preferably about 5 to 25 grams per day per person. Ordinarily 200 to 300 milligrams per kilogram per day are given in divided doses 1 to 6 times a day.

Useful pharmaceutical dosage forms for administration of the polymers of this invention can be illustrated as follows:

TABLETS

Tablets are prepared by conventional procedures so that the dosage unit is 500 milligrams of active ingredient, 150 milligrams of lactose, 50 milligrams of cellulose and 10 milligrams of magnesium stearate.

CAPSULES

Capsules are prepared by conventional procedures so that the dosage unit is 500 milligrams of active ingredient, 100 milligrams of cellulose and 10 milligrams of magnesium stearate.

| Syrup | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | Wt. % |
|---|---|
| Active Ingredient | 10 |
| Sodium Saccharin | 0.01 |
| Keltral ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendible Powder | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | Wt. % |
|---|---|
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | Wt. % |
|---|---|
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | Wt. % |
|---|---|
| Active Ingredient | 30 |
| Tween 80 and Span 80 | 6 |
| Keltrol ® | 0.5 |
| Mineral Oil | 63.5 |

All the ingredients are carefully mixed together to make a homogenous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A cholesterol reducing agent consisting essentially of a copolymer of a monomeric 2-deoxy-streptamine aminoglycosidic antibiotic with a dialdehyde crosslinked to form a reduced polymer containing —$CH_2NH$— bonds, said polymer being formed in the presence of an excess of dialdehyde, or a pharmaceutically acceptable salt thereof.

2. A cholesterol reducing agent of claim 1 wherein the copolymer is a monomeric aminoglycosidic antibiotic selected from a neomycin, a kanamycin, a paromomycin, a gentamycin, and a tobramycin, and the dialdehyde is other than glyoxal.

3. A cholesterol reducing agent of claim 2 wherein the dialdehyde has the formula $OHC(CH_2)_XCHO$ where X is 1–7.

4. A cholesterol reducing agent of claim 3 wherein the dialdehyde is glutaraldehyde.

5. A cholesterol reducing agent of claim 4 wherein the monomeric antibiotic is a neomycin.

6. A cholesterol reducing agent of claim 5 wherein the neomycin is neomycin sulfate.

7. A cholesterol reducing agent of claim 2 characterized in that the copolymer is devoid of antibacterial activity, is insoluble in an aqueous solution of pH 1–8, but is swellable at least two times its original weight.

8. A cholesterol reducing agent consisting essentially of a copolymer of about 1 mole of a neomycin and about 2–6 moles of glutaraldehyde, crosslinked to form a reduced copolymer containing —$CH_2NH$— bonds, or a pharmaceutically acceptable salt thereof.

9. A pharmaceutical composition consisting essentially of a pharmaceutically suitable carrier for oral administration and a cholesterol reducing amount of a copolymer of claim 1.

10. A pharmaceutical composition consisting essentially of a pharmaceutically suitable carrier for oral administration and a cholesterol reducing amount of a copolymer of claim 2.

11. A pharmaceutical composition consisting essentially of a pharmaceutically suitable carrier for oral administration and a cholesterol reducing amount of a copolymer of claim 3.

12. A pharmaceutical composition consisting essentially of a pharmaceutically suitable carrier for oral administration and a cholesterol reducing amount of a copolymer of claim 4.

13. A pharmaceutical composition consisting essentially of a pharmaceutically suitable carrier for oral administration and a cholesterol reducing amount of a copolymer of claim 5.

14. A pharmaceutical composition consisting essentially of a pharmaceutically suitable carrier for oral administration and a cholesterol reducing amount of a copolymer of claim 6.

15. A pharmaceutical composition consisting essentially of a pharmaceutically suitable carrier for oral administration and a cholesterol reducing amount of a copolymer of claim 7.

16. A pharmaceutical composition consisting essentially of a pharmaceutically suitable carrier for oral administration and a cholesterol reducing amount of a copolymer of claim 8.

17. A method of treating hypercholesterolemia in a mammal comprising administering orally to the mammal an effective bile acid binding amount of a copolymer of claim 1.

18. A method of treating hypercholesterolemia in a mammal comprising administering orally to the mammal an effective bile acid binding amount of a copolymer of claim 2.

19. A method of treating hypercholesterolemia in a mammal comprising administering orally to the mammal an effective bile acid binding amount of a copolymer of claim 3.

20. A method of treating hypercholesterolemia in a mammal comprising administering orally to the mammal an effective bile acid binding amount of a copolymer of claim 4.

21. A method of treating hypercholesterolemia in a mammal comprising administering orally to the mammal an effective bile acid binding amount of a copolymer of claim 5.

22. A method of treating hypercholesterolemia in a mammal comprising administering orally to the mammal an effective bile acid binding amount of a copolymer of claim 6.

23. A method of treating hypercholesterolemia in a mammal comprising administering orally to the mammal an effective bile acid binding amount of a copolymer of claim 7.

24. A method of treating hypercholesterolemia in a mammal comprising administering orally to the mammal an effective bile acid binding amount of a copolymer of claim 8.

* * * * *